US009365537B2

(12) United States Patent
Haubs et al.

(10) Patent No.: US 9,365,537 B2
(45) Date of Patent: Jun. 14, 2016

(54) PROCESS FOR RECYCLING POLYACETALS

(71) Applicant: Ticona GMBH, Sulzbach (Taunus) (DE)

(72) Inventors: Michael Haubs, Bad Kreuznach (DE); Jurgen Lingnau, Mainz-Laubenheim (DE); Klaus Kurz, Kelsterbach (DE)

(73) Assignee: Ticona GmbH, Sulzbach (Taunus) (DE)

( * ) Notice: Subject to any disclaimer, the term of this patent is extended or adjusted under 35 U.S.C. 154(b) by 0 days.

(21) Appl. No.: 14/359,333

(22) PCT Filed: Nov. 23, 2012

(86) PCT No.: PCT/EP2012/073544
§ 371 (c)(1),
(2) Date: May 20, 2014

(87) PCT Pub. No.: WO2013/076291
PCT Pub. Date: May 30, 2013

(65) Prior Publication Data
US 2014/0343302 A1 Nov. 20, 2014

(30) Foreign Application Priority Data

Nov. 24, 2011 (EP) .................................... 11190567
Nov. 24, 2011 (EP) .................................... 11190574
Nov. 24, 2011 (EP) .................................... 11190586

(51) Int. Cl.
*C07D 323/06* (2006.01)
*C08G 65/16* (2006.01)
*C07D 323/04* (2006.01)

(52) U.S. Cl.
CPC ............ *C07D 323/06* (2013.01); *C07D 323/04* (2013.01); *C08G 65/16* (2013.01)

(58) Field of Classification Search
USPC .................................. 549/368, 367; 568/613
See application file for complete search history.

(56) References Cited

U.S. PATENT DOCUMENTS

| 3,305,529 | A | 2/1967 | Reynolds et al. |
| 3,457,227 | A | 7/1969 | Kennedy |
| 3,471,998 | A | 10/1969 | Ishida et al. |
| 3,506,615 | A | 4/1970 | Chen |
| 3,697,546 | A | 10/1972 | Asakawa et al. |
| 3,804,808 | A | 4/1974 | Ishii et al. |
| 4,323,502 | A | 4/1982 | Muck et al. |
| 4,330,474 | A | 5/1982 | Nehring |
| 4,358,623 | A | 11/1982 | Murphy et al. |
| 4,420,641 | A | 12/1983 | Gerberich et al. |
| 4,450,301 | A | 5/1984 | McMillan et al. |
| 4,962,235 | A | 10/1990 | Morishita et al. |
| 4,967,014 | A | 10/1990 | Masamoto et al. |
| 5,008,463 | A | 4/1991 | Beck et al. |
| 5,508,448 | A | 4/1996 | Emig et al. |
| 5,767,294 | A | 6/1998 | Steele et al. |
| 6,232,507 | B1 | 5/2001 | Kaiser et al. |
| 6,362,305 | B1 | 3/2002 | Schweers et al. |
| 6,388,102 | B2 | 5/2002 | Schweers et al. |
| 6,448,448 | B1 | 9/2002 | Schweers et al. |
| 6,472,566 | B2 | 10/2002 | Schweers et al. |
| 6,653,487 | B2 | 11/2003 | Schweers et al. |
| 6,781,018 | B2 | 8/2004 | Liu et al. |
| 7,301,055 | B2 | 11/2007 | Hoffmockel et al. |
| 7,390,932 | B2 | 6/2008 | Stroefer et al. |
| 2006/0058537 | A1 | 3/2006 | Haubs et al. |
| 2008/0234459 | A1 | 9/2008 | Lang et al. |
| 2010/0004409 | A1 | 1/2010 | Schwittay et al. |

FOREIGN PATENT DOCUMENTS

| AT | 252913 | 3/1967 |
| DE | 4137846 | 5/1993 |
| DE | 19822598 | 11/1999 |
| GB | 1012372 | 12/1965 |
| GB | 1130513 | 10/1968 |
| GB | 1524440 | 9/1978 |

OTHER PUBLICATIONS

International Search Report and Written Opinion for application PCT/EP2012/073544 dated Apr. 15, 2013.
Yamaguchi T. et al: "Synthesis of cyclooligomers of formaldehyde in liquid sulfur dioxide", Chemistry and Industry, vol. 43, Oct. 23, 1971 pp. 1226-1227, XP008149518, Society of Chemical Industry, London; GB ISSN: 0009-3068.
Shoujin Su, Philippe Zaza and Albert Renken: Catalytic Dehydrogenation of Methanol to Water-Free Formaldehyde, Chem. Eng. Technol. 17 (1994) pp. 34-40.
Co pending U.S. Appl. No. 14/359,223, filed May 19, 2014.
Co pending U.S. Appl. No. 14/359,203, filed May 19, 2014.
Co pending U.S. Appl. No. 14/359,319, filed May 20, 2014.
Co pending U.S. Appl. No. 14/359,308, filed May 20, 2014.
Co pending U.S. Appl. No. 14/359,314, filed May 20, 2014.
Co pending U.S. Appl. No. 14/359,594, filed May 21, 2014.
New Jersey Department of Health and Senior Services, Hazardous Substance Fact Sheet. "Boron Trifluoride Diethyl Etherate." (c) Apr. 2000. Available from : < http://nj.gov/health.eoh/rtkweb/documents/fs/0248.pdf>.

*Primary Examiner* — Kristin Vajda
(74) *Attorney, Agent, or Firm* — Dority & Manning, P.A.

(57) ABSTRACT

A process for recycling polyoxymethylene polymers is disclosed. A polyoxymethylene polymer is at least partially dissolved in an aprotic compound. The resulting solution or suspension (liquid mixture) is then contacted with a catalyst which causes the polyoxymethylene polymer to be converted into a cyclic acetal. The cyclic acetal can be separated, collected and used in other processes. In one embodiment, the cyclic acetal may be used to produce a polyoxymethylene polymer.

18 Claims, No Drawings

PROCESS FOR RECYCLING POLYACETALS

RELATED APPLICATIONS

This present application claims priority to PCT International Patent Application No. PCT/EP2012/073544 having a filing date of Nov. 23, 2012, and which claims filing benefit to European Patent Application No. 11190567.5 filed on Nov. 24, 2011, European Patent Application No. 11190574.1 filed on Nov. 24, 2011, and European Patent Application No. 11190586.5 filed on Nov. 24, 2011, which are all hereby incorporated by reference in their entirety.

BACKGROUND

Oxymethylene polymers, which include polyoxymethylene homopolymers and polyoxymethylene copolymers, possess many useful properties and characteristics. For example, the polymers can have great strength properties while also being chemical resistant. The polymers can also be easily molded into any desired shape. The polymers are currently being used in all different types of applications. For instance, polyoxymethylene polymers are being used to form interior or exterior automotive parts, parts for consumer appliances, parts for industrial processes, and the like.

Oxymethylene polymers can be produced via anionic polymerization of anhydrous formaldehyde or can be produced through the cationic polymerization of formaldehyde or cyclic oligomers, such as trioxane. During cationic polymerization, the polymer can be formed in bulk (i.e. without solvent). Alternatively, the polymerization can take place in solution where the polymer precipitates in a solvent to form a heterogeneous phase. In still another embodiment, a majority of the polymer may be formed in the heterogeneous phase followed by further polymerization in a homogeneous phase.

During the formation of oxymethylene polymers, cationic initiators are typically combined with one or more monomers to initiate polymerization. After polymerization, the reaction mixture can be rapidly and completely deactivated by adding a deactivator.

The deactivator can be added to a heterogeneous phase after the polymer has precipitated in a solvent, or can occur during a homogeneous phase, while the polymer is in a melted form. After being deactivated, the resultant polymer can be ground and/or pelletized. In some embodiments, the polyoxymethylene polymer is compounded with various different components in order to produce a master batch. The master batch can then be combined with greater amounts of polyoxymethylene polymer resin or other ingredients during a molding process to produce various products.

During the production of polyoxymethylene polymers, some scrap material is produced that is comprised primarily of the polyoxymethylene polymer. Since recycling of the waste products coming from production and compounding of the polymer is beneficial, in the past, various different processes have been proposed in order to recycle the polymer. In one embodiment, for instance, the reclaimed polyoxymethylene polymer is converted into an aqueous solution of formaldehyde. The aqueous solution of formaldehyde can then be used to produce various products, such as trioxane. Recycling polyoxymethylene polymers in this manner, however, is not cost effective. In addition, conversion of the polymer into trioxane is relatively low.

In view of the above, a need currently exists for a process of recycling polyoxymethylene polymers. In particular, a need exists for a process for recycling polyoxymethylene polymers and converting them into usable monomers, such as a cyclic acetal.

SUMMARY

In general, the present disclosure is directed to a process for recycling polyoxymethylene polymers. The present disclosure is also directed to a process for producing a cyclic acetal.

In one embodiment, for instance, the present disclosure is directed to a process for the conversion of oxymethylene homo- or copolymers to cyclic acetals comprising the steps:
  a) at least partly dissolving an oxymethylene homo- or copolymer in an liquid medium comprising or consisting of an aprotic compound and
  b) converting the at least partly dissolved oxymethylene homo- or copolymer in the presence of a catalyst to cyclic acetals.

The present disclosure is also directed to a process for the recycling of oxymethylene homo- or copolymers comprising the steps:
  a) at least partly dissolving an oxymethylene homo- or copolymer in an aprotic compound;
  b) converting the at least partly dissolved oxymethylene homo- or copolymer in the presence of a catalyst to cyclic acetals; and
  c) converting the cyclic acetals obtained in step b) optionally together with comonomer(s) to oxymethylene polymers.

In one particular embodiment, the process for producing a cyclic acetal, preferably trioxane and/or tetroxane, comprises:
  preparing a liquid reaction mixture comprising:
    a) 5-70 wt.-%, preferably 20-70 wt.-%, more preferably 30-60 wt.-% of a polyoxymethylene homo- or copolymer;
    b) 25-90 wt.-%, preferably 25-70 wt.-%, more preferably 30-65 wt.-% of an aprotic compound;
    c) 0.001 to 10 wt.-% of a catalyst; and
    d) optionally less than 20 wt.-% of water, wherein the amounts are based on the total weight of the reaction mixture;
  converting the polyoxymethylene homo- or copolymer into a cyclic acetal.

Typically, the reaction is carried out at a temperature higher than about 0° C., preferably ranging from about 0° C. to about 150° C., more preferably ranging from about 10° C. to about 120° C., further preferably from about 20° C. to about 100° C. and most preferably from about 30° C. to about 90° C.

A further advantage of the process of the present invention is that the cyclic acetals can easily be separated from the reaction mixture. The cyclic acetal, especially the trioxane can be separated from the reaction mixture by distillation in a high purity grade. Especially in case aprotic compounds (such as sulfolane) having a boiling point higher than about 20° C. above the boiling point of the cyclic acetals are used the formed cyclic acetals can simply be distilled off. In case sulfolane is used as the aprotic compound the formed trioxane can be distilled off without the formation of an azeotrope of sulfolane with trioxane. The process of the invention can be carried out batch wise or as a continuous process.

In a preferred embodiment the process is carried out as a continuous process wherein the polyoxymethylene polymer is continuously fed to the liquid medium comprising the catalyst and wherein the cyclic acetals, e.g. the trioxane, is continuously separated by separation methods such as distillation.

The process of the invention leads to a lower energy consumption and lower costs for the separation of the cyclic acetals. Due to the high conversion of the polyoxymethylene polymer to the desired cyclic acetals said cyclic acetals can be much more efficiently produced.

According to a preferred embodiment the final conversion of the polyoxymethylene polymer to the cyclic acetal is greater than 10%.

The final conversion refers to the conversion of the polymer into the cyclic acetals in the liquid system. The final conversion corresponds to the maximum conversion achieved in the liquid system.

The final conversion of the polyoxymethylene polymer to the cyclic acetals can be calculated by dividing the amount of cyclic acetals (expressed in wt.-%, based on the total weight of the reaction mixture) in the reaction mixture at the end of the reaction divided by the amount of polymer (expressed in wt.-%, based on the total weight of the reaction mixture) at the beginning of the reaction at t=0.

For example the final conversion can be calculated as:

Final conversion=(amount of trioxane in the reaction mixture expressed in weight-% at the end of the reaction)/(amount of polyoxymethylene polymer in the reaction mixture expressed in weight-% at t=0 [initial amount of polymer in the reaction mixture])

According to a further preferred embodiment of the process of the invention the final conversion of the polymer into the cyclic acetals, preferably trioxane and/or tetroxane, is higher than 12%, preferably higher than 14%, more preferably higher than 16%, further preferably higher than 20%, especially higher than 30%, particularly higher than 50%, for example higher than 80% or higher than 90%.

A further embodiment is a process for producing cyclic acetal comprising
i) preparing a liquid mixture comprising
   a) a polyoxymethylene polymer and
   b) an aprotic compound;
ii) contacting the liquid mixture with a catalyst; and
iii) converting the polyoxymethylene polymer into cyclic acetal, wherein the final conversion of the polymer to said cyclic acetal is greater than 10% on basis of the initial polymer.

According to this preferred embodiment of the present invention a liquid mixture as defined above can be prepared and contacted with a catalyst as defined above. According to a preferred embodiment the catalyst is a solid catalyst which at least remain partly solid under the reaction conditions. Preferably the catalyst is selected from fixed bed catalyst, acid ion-exchange material and solid support carrying Bronsted and/or Lewis acids. Alternatively, the catalyst can be a liquid catalyst which is only partly miscible or essentially immiscible with liquid mixture.

The aprotic compound used in the process may be polar. For instance, in one embodiment, the aprotic compound may be dipolar. In one embodiment, the aprotic compound comprises a sulfur containing organic compound such as a sulfoxide, a sulfone, a sulfonate ester, or mixtures thereof. In one embodiment, the aprotic compound comprises sulfolane.

The aprotic compound may also have a relatively high static permittivity or dielectric constant of greater than about 15. The aprotic compound may also be nitro-group free. In particular, compounds having nitro-groups may form undesired side reactions within the process.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a process for producing one or more cyclic acetals. The process of the present disclosure, for instance, may be used to recycle polyoxymethylene polymers. In particular, according to the present disclosure, a polyoxymethylene polymer is at least partly dissolved in an aprotic solvent. For instance, the polymer can be dissolved in the solvent to form a solution or to form a suspension. In one embodiment, the polymer is dissolved in the solvent at elevated temperatures.

Upon cooling, before the polymer precipitates, a catalyst is contacted with the solution or suspension. In a relatively short amount of time, such as within minutes, the polyoxymethylene polymer can be almost completely converted to a cyclic acetal, such as trioxane and/or tetroxane. The one or more cyclic acetals can then be isolated by evaporation and can be purified through distillation.

In one embodiment, the cyclic acetals are then used to produce further amounts of a polyoxymethylene polymer.

The process of the present disclosure includes many benefits and advantages. For instance, the process can be designed to be highly efficient. For instance, greater than 10%, such as greater than 20%, such as greater than 40%, such as greater than 60%, such as greater than 70%, such as even greater than 90% of the polyoxymethylene polymer may be converted into a cyclic acetal. Further, as mentioned above, the process can occur very rapidly.

As described above, the process can be used to recycle polyoxymethylene polymers that are reclaimed during the production process or during compounding. It should be understood, however, that polyoxymethylene polymers collected from the solid waste stream can also be processed according to the present disclosure.

As described above, the polyoxymethylene polymer is contacted with a catalyst in the presence of an aprotic compound to form a cyclic acetal. The polyoxymethylene polymer may comprise a homopolymer or a copolymer. In one embodiment, the polyoxymethylene homo- and/or copolymer has a number average molecular weight (Mn) of more than 2,000 Dalton.

The aprotic compound or solvent provides various advantages to the process. For example, not only is the aprotic compound a solvent for the polymer, but the aprotic compound also facilitates production of the cyclic acetal in a manner that greatly enhances conversion rates.

Of particular advantage, the cyclic acetal produced according to the process can then be easily separated from the aprotic compound and the catalyst. For instance, in one embodiment, the cyclic acetal can be separated or isolated from the aprotic compound through a simple distillation process, since the aprotic compound may have a much higher boiling point than the cyclic acetal.

In one embodiment, the aprotic compound is a liquid when contacted with the polyoxymethylene polymer. The polyoxymethylene polymer may dissolve into the aprotic compound or may be depolymerized in the aprotic compound to form a homogeneous phase. The aprotic compound and the catalyst, in one embodiment, may comprise a liquid reaction mixture or a liquid medium.

An advantage of the present invention is that the conversion of the polyoxymethylene polymer can be carried out in a liquid system, e.g., a liquid reaction mixture or a liquid medium or a liquid mixture. However, even though it is advantageous, the components of the reaction mixture or the liquid mixture or the liquid medium must not necessarily completely be dissolved. Thus, the reaction mixture or the liquid mixture or liquid medium may also comprise solids or molten components which are not dissolved.

The polyoxymethylene polymer reacts (converts) in the presence of a catalyst. Usually, cationic catalysts, such as Bronsted acids or Lewis acids, accelerate the conversion of the polyoxymethylene polymer to the desired cyclic acetals.

The catalyst is a catalyst for the conversion (reaction) of a polyoxymethylene polymer into cyclic acetals, in particular into trioxane and/or tetroxane.

Cyclic acetals within the meaning of the present disclosure relate to cyclic acetals derived from formaldehyde. Typical representatives are represented the following formula:

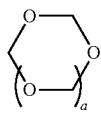

wherein a is an integer ranging from 1 to 3.

Preferably, the cyclic acetals produced by the process of the present disclosure are trioxane (a=1) and/or tetroxane (a=2). Trioxane and tetroxane usually form the major part (at least 80 wt.-%, preferably at least 90 wt.-%) of the cyclic acetals formed by the process of the present disclosure.

The weight ratio of trioxane to tetroxane varies with the catalyst used. Typically, the weight ratio of trioxane to tetroxane ranges from about 3:1 to about 40:1, preferably about 4:1 to about 20:1.

As used herein, an aprotic compound is a compound that does not contain any substantial amounts of hydrogen atoms which can disassociate.

In one embodiment, the aprotic compound is liquid under the reaction conditions. Therefore, the aprotic compound may have a melting point of about 180° C. or less, preferably about 150° C. or less, more preferably about 120° C. or less, especially about 60° C. or less.

For practical reasons, it is advantageous to use an aprotic compound which has a melting point in the order of preference (the lower the melting point the more preferred) of below about 50° C., below about 40° C. and below about 30° C. and below about 20° C. Especially, aprotic compounds which are liquid at about 25 or about 30° C. are suitable since they can be easily transported by pumps within the production plant.

Further, the aprotic compound may have a boiling point of about 120° C. or higher, preferably about 140° C. or higher, more preferably about 160° C. or higher, especially about 180° C. or higher, determined at 1 bar. In a further embodiment the boiling point of the aprotic compound is about 200° C. or higher, preferably about 230° C. or higher, more preferably about 240° C. or higher, further preferably about 250° C. or higher and especially about 260° C. or higher or 270° C. or higher. The higher the boiling point the better the cyclic acetals, especially trioxane and/or tetroxane, formed by the process of the present disclosure can be separated by distillation. Therefore, according to an especially preferred embodiment of the present disclosure the boiling point of the aprotic compound is at least about 20° C. higher than the boiling point of the cyclic acetal formed, in particular at least about 20° C. higher than the boiling point of trioxane and/or tetroxane.

Additionally, aprotic compounds are preferred which do not form an azeotrope with the cyclic acetal, especially do not form an azeotrope with trioxane.

In a preferred embodiment of the present invention the reaction mixture or liquid medium in the reactor 40 comprises at least about 20 wt.-%, preferably at least about 40 wt.-%, more preferably at least about 60 wt.-%, most preferably at least about 80 wt.-% and especially at least about 90 wt.-% of the aprotic compound(s), wherein the weight is based on the total weight of the reaction mixture. The liquid medium or the reaction mixture or the liquid mixture may comprise one or more aprotic compound(s).

In a preferred embodiment the liquid medium is essentially consisting of the aprotic compound. Essentially consisting of means that the liquid medium comprises at least about 95 wt.-%, preferably at least about 98 wt.-%, more preferably at least about 99 wt.-%, especially at least about 99.5 wt.-%, in particular at least about 99.9 wt.-% of the aprotic compound(s). In a further embodiment of the invention the liquid medium is the aprotic compound, i.e., the liquid medium is consisting of the aprotic compound.

It has been found that liquid aprotic compounds which at least partly dissolve or depolymerized the polyoxymethylene polymer lead to excellent results in terms of conversion of the polyoxymethylene polymer into the desired cyclic acetals.

Therefore, aprotic compounds are preferred which at least partly dissolve or depolymerized the polyoxymethylene polymer under the reaction conditions.

The aprotic compound used in the process can be a polar aprotic compound, especially a dipolar compound. Polar aprotic solvents are much more suitable to dissolve the polyoxymethylene polymer. Non-polar aprotic compounds such as unsubstituted hydrocarbons (e.g. cyclic hydrocarbons such as cyclohexane, or alicyclic hydrocarbons such as hexane, octane, decane, etc.) or unsubstituted unsaturated hydrocarbons or unsubstituted aromatic compounds are less suitable. Therefore, according to a preferred embodiment the aprotic compound is not an unsubstituted hydrocarbon or unsubstituted unsaturated hydrocarbon or unsubstituted aromatic compound. Further, preferably the reaction mixture comprises unsubstituted hydrocarbons and/or unsubstituted unsaturated hydrocarbons and/or unsubstituted aromatic compounds in an amount of less than about 50 wt.-%, more preferably less than about 25 wt.-%, further preferably less than about 10 wt.-%, especially less than about 5 wt.-%, e.g. less than about 1 wt.-% or about 0 wt.-%.

Halogen containing compounds are less preferred due to environmental aspects and due to their limited capability to dissolve the polyoxymethylene polymer. Further, the halogenated aliphatic compounds may cause corrosion in vessels or pipes of the plant and it is difficult to separate the cyclic acetals formed from the halogenated compounds.

According to one embodiment, the aprotic compound is halogen free. In a further preferred embodiment the reaction mixture comprises less than about 50 wt.-%, more preferably less than about 25 wt.-%, further preferably less than 10 wt.-%, more preferably less than 5 wt.-%, especially less than 1 wt.-% or 0 wt.-% of halogenated compounds.

Likewise, the use of (liquid) sulphur dioxide leads to difficulties with isolation of the cyclic acetals. Therefore, the aprotic compound is preferably free of sulphur dioxide. In a further preferred embodiment the reaction mixture comprises less than about 50 wt.-%, more preferably less than about 25 wt.-%, further preferably less than 10 wt.-%, more preferably less than 5 wt.-%, especially less than 1 wt.-% or 0 wt.-% of sulphur dioxide.

Polar aprotic compounds are especially preferred. According to a preferred embodiment of the invention the aprotic compound has a relative static permittivity of more than about 15, preferably more than about 16 or more than about 17, further preferably more than about 20, more preferably of more than about 25, especially of more than about 30, determined at 25° C. or in case the aprotic compound has a melting point higher than 25° C. the relative permittivity is determined at the melting point of the aprotic compound.

The relative static permittivity, $\in_r$, can be measured for static electric fields as follows: first the capacitance of a test capacitor $C_0$, is measured with vacuum between its plates. Then, using the same capacitor and distance between its plates the capacitance $C_x$ with an aprotic compound between the plates is measured. The relative dielectric constant can be then calculated as $$\varepsilon_r = \frac{C_x}{C_0}.$$

Within the meaning of the present invention the relative permittivity is determined at 25° C. or in case the aprotic compound has a melting point higher than 25° C. the relative permittivity is determined at the melting point of the aprotic compound.

Preferred are aprotic compounds which dissolve the polyoxymethylene polymer. According to a preferred embodiment the polyoxymethylene polymer is at least partially, preferably at least about 80 wt.-%, more preferably at least about 95 wt.-%, especially completely, in solution in the reaction mixture or liquid mixture.

According to a further aspect of the invention the aprotic compound is a dipolar aprotic compound.

The aprotic compound within the meaning of the present invention is generally a dipolar and non-protogenic compound which has a relative permittivity as defined above of more than 15, preferably more than 25 or more than 30, determined at 25° C. or in case the aprotic compound has a melting point higher than 25° C. the relative permittivity is determined at the melting point of the aprotic compound.

The process can be carried out in manner wherein the polyoxymethylene polymer is completely dissolved or absorbed in the liquid medium or reaction mixture or liquid mixture. Therefore, according to one embodiment the polyoxymethylene polymer and the aprotic compound form a homogenous phase under the reaction conditions.

In one embodiment, the polyoxymethylene polymer and the aprotic compound are combined together and heated in order to dissolve a substantial portion of the polymer. For instance, the aprotic solvent and polymer can be heated to a temperature of greater than about 130° C., such as greater than about 140° C., such as greater than about 150° C., such as greater than about 160° C., such as greater than about 170° C., such as greater than about 180° C., such as greater than about 190° C. The temperature to which the mixture is heated depends in part on the boiling point of the aprotic compound. In one embodiment, for instance, the aprotic compound and polymer are heated to a temperature of from about 150° C. to about 200° C., such as from about 160° C. to about 180° C.

Suitable aprotic compounds are selected from the group consisting of organic sulfoxides, organic sulfones, organic sulfonate ester, and mixtures thereof.

According to a preferred embodiment the aprotic compound is selected from sulfur containing organic compounds.

Further, the aprotic compound is preferably selected from the group consisting of cyclic or alicyclic organic sulfoxides, alicyclic or cyclic sulfones, and mixtures thereof.

Excellent results can be achieved by aprotic compounds as represented by the following formula (I):

wherein
n is an integer ranging from 1 to 6, preferably 2 or 3, and wherein the ring carbon atoms may optionally be substituted by one or more substituents, preferably selected from $C_1$-$C_8$-alkyl which may be branched or unbranched. Preferred compounds of formula (I) are sulfolane, methylsulfolane, dimethylsulfolane, ethylsulfolane, diethylsulfolane, propylsulfolane, dipropylsulfolane, butylsulfolane, dibutylsulfolane, pentylsulfolane, dipentylsulfolane, and hexylsulfolane as well as octylsulfolane.

According to the most preferred embodiment the aprotic compound is sulfolane (tetrahydrothiophene-1,1-dioxide).

Sulfolane is an excellent solvent for the polyoxymethylene polymer, it is stable under acidic conditions, it does not deactivate the catalysts and it does not form an azeotrope with trioxane. Further, it is a solvent which is inert under the reaction conditions.

Unless indicated otherwise the expression "reaction mixture" refers to the mixture which is used for the reaction of the polyoxymethylene polymer to the cyclic acetals. The concentrations and amounts of the individual components of the reaction mixture refer to the concentrations and amounts at the beginning of the reaction. In other words the reaction mixture is defined by the amounts of its starting materials, i.e. the amounts of initial components.

Likewise the amounts defined for the "liquid mixture" refer to the amounts of the components at the beginning of the reaction, i.e. prior to the reaction.

The polyoxymethylene polymer reacts to the cyclic acetals and, as a consequence, the concentration of the polyoxymethylene polymer decreases while the concentration of the cyclic acetals increases.

At the beginning of the reaction a typical reaction mixture of the invention comprises a polyoxymethylene polymer which is at least partly, preferably completely dissolved or absorbed in sulfolane and a catalyst.

Further, an especially preferred embodiment of the present invention is a process for producing cyclic acetal comprising reacting a polyoxymethylene polymer in the presence of a catalyst wherein the reaction is carried out in sulfolane or a process for producing cyclic acetal from a polyoxymethylene polymer in the presence of a catalyst and sulfolane.

A further preferred aprotic compound is represented by formula (II):

wherein $R^1$ and $R^2$ are independently selected from $C_1$-$C_8$-alkyl which may be branched or unbranched, preferably wherein R¹ and R² independently represent methyl or ethyl. Especially preferred is dimethyl sulfone.

According to a further preferred embodiment the aprotic compound is represented by formula (III):

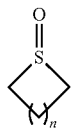

(III)

wherein
n is an integer ranging from 1 to 6, preferably 2 or 3, and wherein the ring carbon atoms may optionally be substituted by one or more substituents, preferably selected from $C_1$-$C_8$-alkyl which may be branched or unbranched.

Suitable aprotic compounds are also represented by formula (IV):

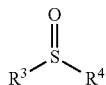

(IV)

wherein $R^3$ and $R^4$ are independently selected from $C_1$-$C_8$-alkyl which may be branched or unbranched, preferably wherein R¹ and R² independently represent methyl or ethyl.

Especially preferred is dimethyl sulfoxide.

Suitable aprotic compounds may be selected from aliphatic dinitriles, preferably adiponitrile.

In a further aspect of the invention a mixture of two or more aprotic compounds is used. A mixture of aprotic compounds may be used to decrease the melting point of the aprotic medium. In a preferred embodiment the aprotic compound comprises or is consisting of a mixture of sulfolane and dimethyl sulfoxide.

The process of the invention is carried out in the presence of a catalyst for the conversion of the polyoxymethylene polymer into cyclic acetals. Suitable catalysts are any components which accelerate the conversion of the polyoxymethylene polymer to the cyclic acetals.

The catalyst is a catalyst for the conversion (reaction) of a polyoxymethylene polymer into cyclic acetals, preferably into trioxane and/or tetroxane.

In one embodiment, although not necessary, the liquid mixture or medium comprising the aprotic compound and the dissolved polymer can be cooled prior to contacting the catalyst. For instance, in one embodiment, the aprotic compound and polymer may be cooled to a temperature of less than about 160° C., such as less than about 150° C., such as less than about 140° C., such as less than about 130° C. For instance, in one embodiment, the liquid reaction mixture may be at a temperature of from about 100° C. to about 140° C. when contacted with the catalyst, such as from about 115° C. to about 135° C.

Usually, cationic catalysts can be used for the process of the invention. The formation of cyclic acetals can be heterogeneously or homogenously catalysed. In case the catalysis is heterogeneous the liquid mixture comprising the polyoxymethylene polymer and the aprotic compound is contacted with the solid catalyst or an immiscible liquid catalyst. A typical liquid immiscible catalyst is a liquid acidic ion exchange resin. Solid catalyst means that the catalyst is at least partly, preferably completely in solid form under the reaction conditions. Typical solid catalysts which may be used for the process of the present invention are acid ion-exchange material, Lewis acids and/or Bronsted acids fixed on a solid support, wherein the support may be an inorganic material such as $SiO_2$ or organic material such as organic polymers.

Preferred catalysts are selected from the group consisting of Bronsted acids and Lewis acids. The catalyst is preferably selected from the group consisting of trifluoromethanesulfonic acid, perchloric acid, methanesulfonic acid, toluenesulfonic acid and sulfuric acid, or derivatives thereof such as anhydrides or esters or any other derivatives that generate the corresponding acid under the reaction conditions. Lewis acids like boron trifluoride, arsenic pentafluoride can also be used. It is also possible to use mixtures of all the individual catalysts mentioned above.

The catalyst is typically used in an amount ranging from about 0.001 to about 15 wt.-%, preferably about 0.01 to about 5 wt.-% or about 0.01 to about 10 wt.-%, more preferably from about 0.05 to about 2 wt.-% and most preferably from about 0.05 to about 0.5 wt.-%, based on the total weight of the reaction mixture.

Advantageously, the aprotic compound does not essentially deactivate the catalyst. Generally, the catalysts used for the formation of cyclic acetals from a polyoxymethylene polymer are cationic catalysts, such as Bronsted acids or Lewis acids. Preferably, under the reaction conditions the aprotic compound does essentially not deactivate the catalyst used in the process of the present invention. Aprotic solvents such as dimethylformamide (DMF), dimethylacetamide (DMAC) or N-methylpyrrolidone (NMP) are too basic and therefore may deactivate the catalyst and, as a consequence, said solvents are less suitable. According to a preferred embodiment of the present invention the liquid reaction mixture is essentially free of amides, preferably essentially free of acylic or cyclic amides. Essentially free means that the amides may be present in an amount of less than about 5 wt.-%, preferably less than about 2 wt.-%, more preferably less than 0.5 wt.-%, especially less than about 0.01 wt.-% and, in particular, less than 0.001 wt.-% or about 0 wt.-%, wherein the weight is based on the total weight of the liquid reaction mixture.

Nitro group containing compounds can lead to undesired side products or even demonstrate an insufficient solubility for the polymers.

Therefore, the aprotic compound preferably does not comprise a nitro group and/or a nitrogen atom. Further, according to a preferred embodiment of the present invention the aprotic compound is a non-aromatic aprotic compound. Especially, the aprotic compound is not nitrobenzene or an aromatic nitro compound. Further, preferably, the aprotic compound does not comprise ether.

Within the meaning of the present invention the aprotic compound does not deactivate the catalyst if under the reaction conditions less than about 95%, preferably less than about 50%, more preferably less than about 10%, of the Bronsted acid catalyst used protonates the aprotic compound. In case a Lewis acid catalyst is used the aprotic compound does not deactivate the catalyst if under the reaction conditions less than about 90 wt.-%, preferably less than about 50 wt.-%, more preferably less than about 10 wt.-% of the Lewis acid catalyst forms a complex with the aprotic compound.

The degree of protonation and complex formation can be determined by NMR spectroscopy such as ¹H or ¹³C-NMR. The degree of protonation and complex formation is determined at 250° C., preferably in $d_6$-DMSO.

The deactivation of the catalyst can also be determined in the following manner:

10 g of commercially available paraformaldehyde (95 wt. %) is dissolved in 100 g of sulfolane at a temperature sufficient to dissolve the paraformaldehyde in such a way that no gaseous formaldehyde can escape. The clear solution is kept at 90° C. and 0.1 wt. % of triflic acid is added. The rate of the formation of trioxane is measured (by measuring the concentration of trioxane as a function of time).

The same experiment is repeated, except that 10 g of the sulfolane are replaced by 10 g of the aprotic compound to be tested. If the rate of trioxane formation is still greater than about 1%, preferably greater than about 5%, more preferably greater than about 10%, of the rate of the initial experiment then it is concluded that the aprotic compound in question does not deactivate the catalyst (even though it may reduce its activity).

The aprotic compound should not be too basic in order to avoid deactivation of the catalysts. On the other hand the aprotic compound preferably does not chemically react with the polyoxymethylene polymer under the reaction conditions, i.e. is an inert aprotic compound.

Preferably, under the reaction conditions the aprotic compound should not react chemically with the polyoxymethylene polymer or the cyclic acetal obtained by the process of the invention. Compounds like water and alcohols are not suitable as they react with formaldehyde. Within the meaning of the present invention an aprotic compound does not chemically react with the polyoxymethylene polymer when it meets the following test criteria: 5 g of commercially available paraformaldehyde (95 wt.-%) is added to 100 g of the aprotic compound containing 0.1 wt.-% trifluoromethanesulfonic acid and heated at 120° C. for 1 hour with stirring in a closed vessel so that no gaseous formaldehyde can escape. If less than about 1 wt.-%, preferably less than about 0.5 wt.-%, more preferably less than about 0.1 wt.-% and most preferably less than about 0.01 wt.-% of the aprotic compound has chemically reacted, then the aprotic compound is considered not to have reacted with the polyoxymethylene polymer. If the aprotic compound meets the criteria it is considered inert.

Further, under the acidic reaction conditions the aprotic compound should be essentially stable. Therefore, aliphatic ethers or acetals are less suitable as aprotic compounds. The aprotic compound is considered stable under acidic conditions within the meaning of the present invention if the aprotic compound meets the following test conditions:

100 g of the aprotic compound to be tested containing 0.5% by weight (wt.-%) trifluoromethanesulfonic acid is heated at 120° C. for 1 hour. If less than about 0.5 wt.-%, preferably less than about 0.05 wt.-%, more preferably less than about 0.01 wt.-% and most preferably less than about 0.001 wt.-% of the aprotic compound has chemically reacted, then the aprotic compound is considered to be stable under acidic conditions.

Preferably, the reaction mixture comprises the polyoxymethylene polymer in an amount ranging from about 0.1 to about 80 wt.-% or about 1 to less than about 80 wt.-%, more preferably from about 5 to about 75 wt.-%, further preferably ranging from about 10 to about 70 wt.-% and most preferred ranging from about 20 to about 70 wt.-%, especially ranging from 30 to 60 wt.-% based on the total weight of the reaction mixture.

It has been found that especially good results in terms of conversion can be achieved when the polyoxymethylene polymer is dissolved in a high concentration in the aprotic compound.

Therefore, in a further aspect the amount of polyoxymethylene polymer is at least 5 wt.-% or at least 10 wt.-%, preferably ranging from 5 to 75 wt.-%, further preferably 10 to 70 wt.-%, especially 15 to 60 wt.-%, based on the total weight of the homogeneous or heterogeneous liquid mixture consisting of the polyoxymethylene polymer and the aprotic compound.

According to a preferred embodiment the weight ratio of polyoxymethylene polymer to aprotic compound is ranging from about 1:1000 to about 4:1, preferably about 1:600 to about 3:1, more preferably about 1:400 to about 2:1, further preferably about 1:200 to about 1:1, especially preferably about 1:100 to about 1:2, particularly about 1:50 to about 1:3, for example about 1:20 to about 1:6 or about 1:15 to about 1:8.

Typically, the reaction is carried out at a temperature higher than about 0° C., preferably ranging from about 0° C. to about 150° C., more preferably ranging from about 10° C. to about 120° C.

The pressure during the reaction can generally be from about 10 millibars to about 20 bars, such as from about 0.5 bar to about 10 bar, such as from about 0.5 bar to about 2 bar.

A further advantageous of the process of the present invention is that the cyclic acetals can easily be separated from the reaction mixture. The cyclic acetal, especially the trioxane can be separated from the reaction mixture by distillation in a high purity grade. Especially in case aprotic compounds (such as sulfolane) having a boiling point higher than about 20° C. above the boiling point of the cyclic acetals is used the formed cyclic acetals can simply be distilled off. In case sulfolane is used as the aprotic compound the formed trioxane can be distilled off without the formation of an azeotrope of sulfolane with trioxane. The process of the invention can be carried out batch wise or as a continuous process.

In a preferred embodiment the process is carried out as a continuous process wherein the polyoxymethylene polymer is continuously fed to the liquid medium comprising the catalyst and wherein the cyclic acetals, e.g. the trioxane, is continuously separated (isolated) by separation methods such as distillation.

The process of the invention leads to an extremely high conversion of the polyoxymethylene polymer to the desired cyclic acetals.

According to a preferred embodiment the final conversion of the polyoxymethylene polymer to the cyclic acetal is greater than 10%, based on initial polyoxymethylene polymer.

The final conversion refers to the conversion of the polyoxymethylene polymer into the cyclic acetals in the liquid system. The final conversion corresponds to the maximum conversion achieved in the liquid system.

The final conversion of the polyoxymethylene polymer to the cyclic acetals can be calculated by dividing the amount of cyclic acetals (expressed in wt.-%, based on the total weight of the reaction mixture) in the reaction mixture at the end of the reaction divided by the amount of polyoxymethylene polymer (expressed in wt.-%, based on the total weight of the reaction mixture) at the beginning of the reaction at t=0.

For example the final conversion of the polyoxymethylene polymer to trioxane can be calculated as:

Final conversion=(amount of trioxane in the reaction mixture expressed in weight-% at the end of the reaction)/(amount of polyoxymethylene polymer in the reaction mixture expressed in weight-% at t=0 [initial amount of polyoxymethylene polymer in the reaction mixture])

According to a further preferred embodiment of the process of the invention the final conversion of the polyoxymethylene polymer into the cyclic acetals, preferably trioxane and/or tetroxane, is higher than 12%, preferably higher than 14%, more preferably higher than 16%, further preferably higher than 20%, especially higher than 30%, particularly higher than 50%, for example higher than 80% or higher than 90%.

According to a further preferred embodiment of the process of the invention the conversion of the polyoxymethylene polymer into the cyclic acetals, preferably trioxane and/or tetroxane, is higher than 12%, preferably higher than 14%, more preferably higher than 16%, further preferably higher than 20%, especially higher than 30%, particularly higher than 50%, for example higher than 80% or higher than 90%.

As described above, the process of the present disclosure converts a polyoxymethylene polymer into one or more cyclic acetals. The resulting cyclic acetals can be used in numerous and diverse applications. In one embodiment, for instance, the cyclic acetals produced through the process may then be used to produce a thermoplastic polymer, such as a polyoxymethylene polymer. Thus, in one embodiment, reclaimed polyoxymethylene polymers are converted into a cyclic acetal which is then used as a monomer to produce further amounts of a polyoxymethylene polymer.

The oxymethylene polymer production process may comprise any suitable process for producing oxymethylene homopolymers and/or copolymers. The polymer production process, for instance, may comprise an anionic polymerization process or a cationic polymerization process. The process for producing the oxymethylene polymer may comprise a heterogeneous process where the polymer precipitates in a liquid, may comprise a homogeneous process such as a bulk polymerization process that forms a molten polymer or may be a polymer process that includes both a heterogeneous phase and a homogeneous phase.

For the preparation of oxymethylene polymers, a monomer that forms —$CH_2$—O— units or a mixture of different monomers, are reacted in the presence of an initiator. Examples of monomers that form —$CH_2$O-units are formaldehyde or its cyclic oligomers, such as 1,3,5-trioxane(trioxane) or 1,3,5,7-tetraoxocane.

The oxymethylene polymers are generally unbranched linear polymers which generally contain at least 80 mol %, preferably at least 90 mol %, in particular at least 95 mol %, of oxymethylene units (—$CH_2$—O—). Alongside these, the oxymethylene polymers contain —$(CH_2)_x$—O— units, where x can assume the values from 2 to 25. Small amounts of branching agents can be used if desired. Examples of branching agents used are alcohols whose functionality is three or higher, or their derivatives, preferably tri- to hexahydric alcohols or their derivatives. Preferred derivatives are formulas in which, respectively, two OH groups have been reacted with formaldehyde, other branching agents include monofunctional and/or polyfunctional glycidyl compounds, such as glycidyl ethers. The amount of branching agents is usually not more than 1% by weight, based on the total amount of monomer used for the preparation of the oxymethylene polymers, preferably not more than 0.3% by weight.

Oxymethylene polymers can also contain hydroxyalkylene end groups —O—$(CH_2)_x$—OH, alongside methoxy end groups, where x can assume the values from 2 to 25. These polymers can be prepared by carrying out the polymerization in the presence of diols of the general formula HO—$(CH_2)_x$—OH, where x can assume the values from 2 to 25. The polymerization in the presence of the diols leads, via chain transfer, to polymers having hydroxyalkylene end groups. The concentration of the diols in the reaction mixture depends on the percentage of the end groups intended to be present in the form of —O—$(CH_2)_x$—OH, and is from 10 ppm by weight to 2 percent by weight.

The molecular weights of these polymers, expressed via the volume melt index MVR, can be adjusted within a wide range. The polymers typically have repeat structural units of the formula —$(CH_2$—O—$)_n$—, where n indicates the average degree of polymerization (number average) and preferably varies in the range from 100 to 10 000, in particular from 500 to 4000.

Oxymethylene polymers can be prepared in which at least 80%, preferably at least 90%, particularly preferably at least 95%, of all of the end groups are alkyl ether groups, in particular methoxy or ethoxy groups.

Comonomers that may be used to produce oxymethylene copolymers including cyclic ethers or cyclic formals. Examples include, for instance, 1,3-dioxolane, diethylene glycol formal, 1,4-butanediol formal, ethylene oxide, propylene 1,2-oxide, butylene 1,2-oxide, butylene 1,3-oxide, 1,3 dioxane, 1,3,6-trioxocane, and the like. In general, one or more of the above comonomers may be present in an amount from about 0.1 to about 20 mol %, such as from about 0.2 to about 10 mol %, based on the amount of trioxane.

The molecular weight of the resultant homo- and copolymers can be adjusted via use of acetals of formaldehyde (chain transfer agents). These also lead to production of etherified end groups of the polymers, and a separate reaction with capping reagents can therefore be omitted. Chain transfer agents used are monomeric or oligomeric acetals of formaldehyde. Preferred chain transfer agents are compounds of the formula I $$R^1—(O—CH_2)_q—O—R^2 \qquad (I),$$

in which $R^1$ and $R^2$, independently of one another, are monovalent organic radicals, preferably alkyl radicals, such as butyl, propyl, ethyl, and in particular methyl, and q is a whole number from 1 to 50.

Particularly preferred chain transfer agents are compounds of the formula I, in which q=1, very particularly preferably methylal. The amounts used of the chain transfer agents are usually up to 5000 ppm, preferably from 100 to 3000 ppm, based on the monomer (mixture).

The initiators used can comprise the cationic initiators usually used in the preparation of oxymethylene homo- and copolymers. Examples of these are protic acids, e.g. fluorinated or chlorinated alkyl- and arylsulfonic acids, such as trifluoromethanesulfonic acid, trifluoromethanesulfonic anhydride, or Lewis acids, such as stannic tetrachloride, arsenic pentafluoride, phosphorus pentafluoride, and boron trifluoride, and also their complex compounds, e.g. boron trifluoride etherate, and carbocation sources, such as triphenylmethyl hexafluorophosphate.

In one embodiment, the initiator for cationic polymerization is an isopoly acid or a heteropolyacid or an acid salt thereof which may be dissolved in an alkyl ester of a polybasic carboxylic acid.

The heteropoly acid is a generic term for polyacids formed by the condensation of different kinds of oxo acids through dehydration and contains a mono- or poly-nuclear complex ion wherein a hetero element is present in the center and the oxo acid residues are condensed through oxygen atoms. Such a heteropoly acid is represented by formula (1):

$$H_x[M_mM'_nO_z]·yH_2O \qquad (1)$$

wherein
M represents an element selected from the group consisting of P, Si, Ge, Sn, As, Sb, U, Mn, Re, Cu, Ni, Ti, Co, Fe, Cr, Th and Ce,
M' represents an element selected from the group consisting of W, Mo, V and Nb, m is 1 to 10,
n is 6 to 40,
z is 10 to 100,
x is an integer of 1 or above, and
y is 0 to 50.

In another embodiment, the initiator for cationic polymerization comprises at least one protic acid and at least one salt of a protic acid, wherein said at least one protic acid is sulfuric acid, tetrafluoroboric acid, perchloric acid, fluorinated alkyl sulfonic acid, chlorinated alkyl sulfonic acid or aryl sulfonic acid, and wherein said salt of protic acid is an alkali metal or alkaline earth metal salt of protic acid and/or a substituted ammonium salt of protic acid, the cations of the ammonium salt having the general formula (I)

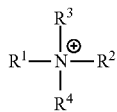

(I)

where $R^1$-$R^4$ are independently hydrogen, an alkyl group or an aryl group.

Particular preference is given to substituted ammonium ions having the general formula (I)

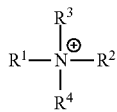

(I)

where $R^1$ to $R^4$ are independently hydrogen, an alkyl group such as methyl, ethyl, n-propyl, isopropyl, n-butyl, isobutyl or an aryl group such as phenyl or 4-methoxypheny.

In order to terminate the polymerization, the reaction mixture, which still comprises unconverted monomers and/or byproducts, such as trioxane and formaldehyde, alongside polymer, is brought into contact with deactivators. These can be added in bulk form or a form diluted with an inert solvent to the polymerization mixture. The result is rapid and complete deactivation of the active chain ends.

Deactivators that can be used are those compounds which react with the active chain ends in such a way as to terminate the polymerization reaction. Examples are the organic bases triethylamine or melamine, and also the inorganic bases potassium carbonate or sodium acetate. It is also possible to use very weak organic bases, such as carboxamides, e.g. dimethylformamide. Tertiary bases are particularly preferred, examples being triethylamine and hexamethylmelamine.

The present disclosure may be better understood with respect to the following examples.

EXAMPLES

Example 1

10 g of dried Polyoxymethylene Copolymer (with a low Dioxolane content) (TICONA trade name: Hostaform® HS 15) with melt index of 1.5 g/10 min were dissolved in 90 g of sulfolane at 145° C. with stirring. The clear solution was added to 20 g sulfolane (at 120° C.) containing 0.4 ml of a 10 wt % solution of triflic acid in sulfolane. After the addition was completed, the homogeneous solution was cooled to 60° C., neutralized with triethylamine and then analyzed. The following composition was found:
Trioxane: 7.1 wt %
Tetroxane: 0.75 wt %
Formaldehyde: 0.4 wt %
Methylformate: <20 ppm Example 2

Example 1 was repeated, except that perchloric acid (70 wt % in water) was used for triflic acid:
10 g of dried Polyoxymethylene Copolymer (with a low Dioxolane content) (TICONA trade name: Hostaform® HS 15) with melt index of 1.5 g/10 min were dissolved in 90 g of sulfolane at 145° C. with stirring. The clear solution was added to 20 g sulfolane (at 120° C.) containing 1.2 ml of a 2 wt % solution of perchloric acid (70 wt % in water) in sulfolane. After the addition was completed, the homogeneous solution was cooled to 60° C., neutralized with triethylamine and then analyzed. The following composition was found:
Trioxane: 7.2 wt %
Tetroxane: 0.8 wt %
Formaldehyde: 0.3 wt %
Methylformate: <20 ppm Comparative Example 3

Example 1 was repeated, except that nitrobenzene was used for sulfolane as a solvent:
10 g of dried Polyoxymethylene Copolymer (with a low Dioxolane content) (TICONA trade name: Hostaform® HS 15) with melt index of 1.5 g/10 min were dissolved in 90 g of nitrobenzene at 145° C. with stirring. The clear solution was added to 20 g nitrobenzene (at 120° C.) containing 0.4 ml of a 10 wt % solution of triflic acid in sulfolane. After the addition was completed, the homogeneous solution was cooled to 60° C., neutralized with triethylamine and then analyzed. The following composition was found:
Trioxane: 6.2 wt %
Tetroxane: 0.7 wt %
Formaldehyde: 0.7 wt %
Methylformate: 0.5 wt %

The GC spectrum also showed a new peak with a retention time beyond that of nitrobenzene, which was not further analyzed but is believed to be a reaction product of nitrobenzene with formaldehyde. Thus, nitrobenzene is not stable under reaction conditions, produces side products (methylformate) and consequently has a lower yield in trioxane.

Example 4

Example 1 was repeated, except that a mixture of Dimethylsulfone (30 g) and Sulfolane (60 g) was used for sulfolane as a solvent:
10 g of dried Polyoxymethylene Copolymer (with a low Dioxolane content) (TICONA trade name: Hostaform® HS 15) with melt index of 1.5 g/10 min were dissolved in a mixture of Dimethylsulfone (30 g) and Sulfolane (60 g) at 145° C. with stirring. The clear solution was added to 20 g sulfolane (at 120° C.) containing 0.4 ml of a 10 wt % solution of triflic acid in sulfolane. After the addition was completed, the homogeneous solution was cooled to 60° C., neutralized with triethylamine and then analyzed. The following composition was found:
Trioxane: 7.1 wt %
Tetroxane: 0.6 wt %
Formaldehyde: 0.8 wt %
Methylformate: 9.4 ppm

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for the conversion of oxymethylene homo- or copolymers to cyclic acetals comprising the steps:
    a) at least partly dissolving an oxymethylene homo- or copolymer in a liquid medium comprising an aprotic compound, the aprotic compound having boiling point of 120° C. or higher, determined at 1 bar; and
    b) converting the at least partly dissolved oxymethylene homo- or copolymer in the presence of a catalyst to cyclic acetals.

2. A process according to claim 1, wherein at least 20 wt.-% of the oxymethylene homo- or copolymer is dissolved in the aprotic compound.

3. A process according to claim 1 wherein the oxymethylene polymer is at least partly dissolved at a temperature higher than 100° C.

4. A process for the conversion of oxymethylene homo- or copolymers to cyclic acetals comprising the steps:
    a) at least partly dissolving an oxymethylene homo- or copolymer in a liquid medium comprising an aprotic compound; and
    b) converting the at least partly dissolved oxymethylene homo- or copolymer in the presence of a catalyst to cyclic acetals; and
    wherein the cyclic acetals obtained are purified or separated.

5. A process according to claim 1 wherein the aprotic compound is liquid under the dissolution condition.

6. A process for the conversion of oxymethylene homo- or copolymers to cyclic acetals comprising the steps:
    a) at least partly dissolving an oxymethylene homo- or copolymer in a liquid medium comprising an aprotic compound, and wherein the polyoxymethylene homo- or copolymer has a number average molecular weight (Mn) of more than 2,000 Dalton; and
    b) converting the at least partly dissolved oxymethylene homo- or copolymer in the presence of a catalyst to cyclic acetals.

7. A process according to claim 6 wherein the aprotic compound has a boiling point of 120° C. or higher, determined at 1 bar.

8. A process according to claim 1 wherein the oxymethylene polymer, the aprotic compound and the catalyst form a reaction mixture and wherein the reaction mixture comprises at least 60 wt.-% of the aprotic compound, wherein the weight is based on the total weight of the reaction mixture.

9. A process according to claim 1 wherein the aprotic compound comprises a sulfur containing organic compound.

10. A process according to claim 1 wherein the aprotic compound comprises a dipolar nitro-group free compound.

11. A process according to claim 1 wherein the aprotic compound is represented by formula (I):

(I)

wherein
n is an integer ranging from 1 to 6, and
wherein the ring carbon atoms may optionally be substituted by one or more substituents, selected from $C_1$-$C_8$-alkyl which may be branched or unbranched.

12. A process according to claim 1 wherein the aprotic compound is sulfolane.

13. A process according to claim 1 wherein the aprotic compound is represented by formula (II):

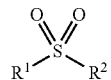

(II)

wherein $R^1$ and $R^2$ are independently selected from $C_1$-$C_8$-alkyl which may be branched or unbranched.

14. A process according to claim 1 wherein the aprotic compound is represented by formula (III):

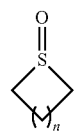

(III)

wherein
n is an integer ranging from 1 to 6, and
wherein the ring carbon atoms may optionally be substituted by one or more substituents, selected from $C_1$-$C_8$-alkyl which may be branched or unbranched; or
the aprotic compound is represented by formula (IV):

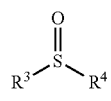

(IV)

wherein $R^3$ and $R^4$ are independently selected from $C_1$-$C_8$-alkyl which may be branched or unbranched.

15. A process according to claim 1 wherein the conversion to the cyclic acetal is carried out at a temperature ranging from 40° C. to 130° C. and is carried out at a pressure of from 10 millibars to 10 bars.

16. A process according to claim 1, wherein higher than 30 percent of the oxymethylene homo- or copolymer is converted into the cyclic acetal.

17. A process according to claim 1, further comprising the step of converting the cyclic acetals formed during the process into an oxymethylene polymer.

18. A process according to claim 1, wherein the oxymethylene homo- or copolymer is at least partly dissolved in the aprotic compound while being heated and wherein the resulting liquid medium is cooled prior to being contacted with the catalyst.

* * * * *